(12) United States Patent
Hitt et al.

(10) Patent No.: US 9,724,344 B2
(45) Date of Patent: *Aug. 8, 2017

(54) ENHANCED DELIVERY OF DRUG COMPOSITIONS TO TREAT LIFE THREATENING INFECTIONS

(71) Applicant: BOARD OF REGENTS, THE UNIVERSITY OF TEXAS SYSTEM, Austin, TX (US)

(72) Inventors: James E. Hitt, Midland, MI (US); True L. Rogers, Midland, MI (US); Brian D. Scherzer, Midland, MI (US); Ian B. Gillespie, Linden, MI (US); Paula C. Garcia, Midland, MI (US); Nicholas S. Beck, Midland, MI (US); Christopher J. Tucker, Midland, MI (US); Timothy J. Young, Bay City, MI (US); David A. Hayes, Midland, MI (US); Robert O. Williams, III, Austin, TX (US); Keith P. Johnston, Austin, TX (US); Jason T. McConville, Austin, TX (US); Jay I. Peters, San Antonio, TX (US); Robert Talbert, San Antonio, TX (US); David S. Burgess, San Antonio, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 54 days.

This patent is subject to a terminal disclaimer.

(21) Appl. No.: 14/713,156

(22) Filed: May 15, 2015

(65) Prior Publication Data

US 2015/0320740 A1 Nov. 12, 2015

Related U.S. Application Data

(63) Continuation of application No. 11/660,012, filed as application No. PCT/US2005/030543 on Aug. 26, 2005, now Pat. No. 9,061,027.

(60) Provisional application No. 60/605,179, filed on Aug. 27, 2004.

(51) Int. Cl.
*A61K 31/496* (2006.01)
*A61K 9/00* (2006.01)
*A61K 9/19* (2006.01)

(52) U.S. Cl.
CPC ............ *A61K 31/496* (2013.01); *A61K 9/008* (2013.01); *A61K 9/0073* (2013.01); *A61K 9/19* (2013.01)

(58) Field of Classification Search
CPC ........ A61K 31/496; A61K 9/008; A61K 9/19; A61K 9/0073
See application file for complete search history.

(56) References Cited

U.S. PATENT DOCUMENTS

| | | | |
|---|---|---|---|
| 4,950,477 A | 8/1990 | Schmitt et al. | |
| 5,145,684 A | 9/1992 | Liversidge et al. | |
| 5,539,021 A | 7/1996 | Pate et al. | |
| 5,688,842 A | 11/1997 | Pate, III et al. | |
| 6,264,922 B1 | 7/2001 | Wood et al. | |
| 6,630,169 B1 | 10/2003 | Bot et al. | |
| 6,756,062 B2 | 6/2004 | Johnston et al. | |
| 6,862,890 B2 | 3/2005 | Williams, III et al. | |
| 2002/0081334 A1 | 6/2002 | Johnston et al. | |
| 2002/0102294 A1 | 8/2002 | Bosch et al. | |
| 2003/0041602 A1 | 3/2003 | Williams, III et al. | |
| 2003/0049323 A1 | 3/2003 | Hitt et al. | |
| 2003/0068280 A1 | 4/2003 | Bannister et al. | |
| 2003/0072807 A1 | 4/2003 | Wong et al. | |
| 2003/0077329 A1 | 4/2003 | Kipp et al. | |
| 2004/0022862 A1 | 2/2004 | Kipp et al. | |
| 2004/0105821 A1* | 6/2004 | Bernstein ............. | A61K 9/0075 424/46 |
| 2004/0121003 A1 | 6/2004 | Chickering et al. | |
| 2004/0137070 A1 | 7/2004 | Scherzer et al. | |
| 2004/0176391 A1 | 9/2004 | Weers et al. | |
| 2010/0047340 A1 | 2/2010 | McGinity et al. | |

FOREIGN PATENT DOCUMENTS

| | | |
|---|---|---|
| DE | 101 45 361 | 4/2003 |
| GB | 2387781 | 10/2003 |
| WO | WO 90/11754 | 10/1990 |
| WO | WO 02/054868 | 7/2002 |
| WO | WO 2004/060351 | 7/2004 |
| WO | WO 2004/060903 | 7/2004 |

OTHER PUBLICATIONS

"Inhalation Aerosols," edited by A. J. Hickey, Marcel, New York, pp. 505-509, 1996.
Boogaerts et al., "Clinical experience with itraconazole in systemic fungal infections," *Drugs*, 61(Suppl. 1):39-47, 2001.
Chen et al., "Preparation of cyclosporine A nanoparticles by evaporative precipitation into aqueous solution," *Int. J. Pharmaceutics*, 242(1-2):3-14, 2002.
Derwent Abstract No. 2004-215434, DE 10145361, 2004.
Edwards et al., "Large porous particles for pulmonary drug delivery," *Science*, 276(5320):1868-1871, 1997.
Finlay, The Mechanics of Inhaled Pharmaceutical Aerosols: An Introduction, Academic Press, 2001.
Gallis et al., "Amphotericin B: 30 years of clinical experience," *Rev. Int. Dis.*, 12(2):308-329, 1990.

(Continued)

*Primary Examiner* — Jonathan S Lau
(74) *Attorney, Agent, or Firm* — Parker Highlander, PLLC

(57) ABSTRACT

Inhalable compositions are described. The inhalable compositions comprise one or more respirable aggregates, the respirable aggregates comprising one or more poorly water soluble active agents, wherein at least one of the active agents reaches a maximum lung concentration ($C_{max}$) of at least about 0.25 µg/gram of lung tissue and remains at such concentration for a period of at least one hour after being delivered to the lung. Methods for making such compositions and methods for using such compositions are also disclosed.

10 Claims, 5 Drawing Sheets

(56) References Cited

OTHER PUBLICATIONS

Grant et al., "Itraconazole. A review of its pharmacodynamic and pharmacokinetic properties, and therapeutic use in superficial and systemic mycoses," *Drugs*, 37(3):310-344, 1989.

Hu et al., "Improvement of dissolution rates of poorly water soluble APIs using novel spray freezing into liquid technology," *Pharmaceutical Research*, 19(9):1278-1284, 2002.

Jones, "Investigation of pulmonary and oral delivery of itraconazole produced by evaporative precipitation into aqueous solution (EPAS) and spay-freezing into liquid (SFL) technology in a murine model," doctoral dissertation, the University of Texas, May 2003.

Lieberman et al., In: Pharmaceutical Dosage Forms—Disperse Systems, M. Dekker, Inc., $2^{nd}$ Edition, vol. 2, pp. 1-46, 1996.

Lin et al., "Aspergillosis case-fatality rate: systematic review of the literature," *Clin. Inf. Diseases*, 32(3):358-366, 2001.

Loeffler et al., "Antifungal drug resistance," *Clin. Infect. Diseases*, 36(Suppl. 1):S31-S41, 2003.

Lowell et al., In: Powder Surface Area and Porosity, Chapman & Hall, $3^{rd}$ Edition, pp. 4-6, 1991.

McConville et al., "Nebulisation of a suspension containing itraconazole prepared by evaporative precipitation into aqueous solution," poster presentation at the 2003 AAPS Annual Meeting and Exposition; Oct. 2003; Poser T3242.

McConville et al., "Spay freezing into liquid of itraconazole for pulmonary delivery," poser presentation at the 2003 AAPS Annual Meeting and Exposition; Oct. 2003; Poser T3243.

Mehrad et al., "Spectrum of Aspergillus infection in lung transplant recipients: case series and review of the literature," *Chest*, 119(1):169-175, 2001.

Meis et al., "Current management of fungal infections," *Drugs*, 61(Suppl. 1):13-25, 2001.

Mendelson, "Fungal infections in the immunocompromised," *Microbiology Today*, 28(2):10-12, 2001.

Office Communication issued in U.S. Appl. No. 11/660,012, dated Feb. 17, 2015.

Office Communication issued in U.S. Appl. No. 11/660,012, dated Jul. 25, 2014.

Office Communication issued in U.S. Appl. No. 11/660,012, dated Oct. 25, 2013.

Office Communication issued in U.S. Appl. No. 11/660,012, dated May 6, 2013.

Office Communication issued in U.S. Appl. No. 11/660,012, dated Apr. 29, 2011.

Office Communication issued in U.S. Appl. No. 11/660,012, dated Feb. 10, 2011.

Office Communication issued in U.S. Appl. No. 11/660,012, dated Aug. 17, 2010.

Office Communication issued in U.S. Appl. No. 11/660,012, dated Jul. 6, 2010.

Office Communication issued in U.S. Appl. No. 11/660,012, dated Mar. 9, 2010.

Overhoff et al., "Use of thin film freezing to enable drug delivery: a review," *J. Drug. Del. Sci. Tech.*, 19(2):89-98, 2009.

PCT International Search Report issued in International Patent Application No. PCT/US2005/030543, dated Jan. 25, 2006.

Pfaller et al., "In vitro susceptibility testing of filamentous fungi: comparison of Etest and reference microdilution methods for determining itraconazole MICs," *J. Clin. Microbiol.*, 38(9):3359-3361, 2000.

Rogers et al., "A novel particle engineering technology to enhance dissolution of poorly water soluble drugs: spray-freezing into liquid," *European J. of Pharmaceutics and Biopharmaceutics*, 54(3):271-280, 2002.

Rogers et al., "A novel particle engineering technology: spray-freezing into liquid," *Int. J. of Pharmaceuticeutics*, 242(1-2):93-100, 2002.

Sarkari et al., "Enhanced drug dissolution using evaporative precipitation into aqueous solution," *Int. J. Pharmaceutics*, 243:17-31, 2002.

Six et al., "Characterization of solid dispersions of itraconazole and hydroxypropylmethylcellulose prepared by melt extrusion, Part II," *Pharm. Res.*, 20(7):1047-1054, 2003.

Wilson et al., "The direct cost and incidence of systemic fungal infections," *Value in Health*, 5(1):526-34, 2002.

Yong et al., "Rapid expansion from supercritical to aqueous solution to produce submicron suspensions of water-insoluble drugs," *Biotechnol. Prog.*, 16(3):402-407, 2000.

\* cited by examiner

ENHANCED DELIVERY OF DRUG COMPOSITIONS TO TREAT LIFE THREATENING INFECTIONS

The present application is a continuation of U.S. application Ser. No. 11/660,012, filed Feb. 9, 2007, as a national phase application under 35 U.S.C. §371 of International Application No. PCT/US05/30543, filed Aug. 26, 2005, which claims benefit of priority to U.S. Provisional Application No. 60/605,179, filed Aug. 27, 2004.

The invention relates to compositions and methods for delivering poorly water soluble drug compositions made by particle engineering processes, and more particularly, to nanoparticles of active agents and methods of making the same.

BACKGROUND OF THE INVENTION

Without limiting the scope of the invention, its background is described in connection with mechanical micronization processes or solution-based phase separation processes, as an example. Micronization procedures can modify particle size, porosity and density, and the active agent may be mixed with pharmaceutical excipients using small particle technologies to maximize delivery to the desired target for drug administration.

Delivery of a therapeutic agent to the respiratory tract is important for the treatment of local and/or systemic diseases; however, using conventional techniques for delivery of agents to the lung has proven extremely inefficient. Attempts to develop respirable micronized suspensions of poorly soluble compounds have also failed because the particles are too large to be delivered by aerosolized aqueous droplets and fail to release the drug efficiently. Using these techniques only about 10 to 20% of the agent reaches the lung due to losses to the device used to deliver the agent, loss to the mouth and throat, and exhalation.

The relative rate of absorption and residence time of the therapeutic agent must also be considered for determining the amount of therapeutic agent that reaches the site of action. Since the vast majority of the available surface area of the lung for drug delivery is located in the deep lung, delivery to the lung may best be realized with delivery of the particles to the peripheral alveoli of the deep lung. In contrast, particles deposited in the upper respiratory tract are rapidly removed by the mucociliary escalator, subsequently transported to the throat and either swallowed or removed by coughing. While delivery to the deep lung is required for efficient delivery, the particles must also be able to release their content to be effective.

Particle formation technologies may be classified as either mechanical micronization processes or solution-based phase separation processes. Mechanical micronization methods include milling techniques such as that cited in, e.g., U.S. Pat. No. 5,145,684, however, friction generated during these milling processes may lead to either thermal or mechanical degradation of the active agent. Spray drying, another common method used to micronize drug substances, can cause difficulty with respect to capturing the particles that are formed when such particles are relatively small.

Systemic fungal infections are a major cause of morbidity and mortality in the immunocompromised patient. The most common infections in this group are candidiasis and aspergillosis, especially in the case of acute invasive fungal infections. For patients infected with aspergillosis the prognosis is very poor. Mortality rates are as high as 49% for patients undergoing chemotherapy treatment for cancers such as leukemia and lymphoma, while HIV/AIDS patients have one of the highest mortality rates at 86%. The use of antimicrobial drugs (e.g., antibiotics) for the treatment of a variety of underlying medical conditions also promotes the incidence of invasive fungal infection. Lung transplant recipients are uniquely susceptible to infection due to the fact that the lungs are constantly exposed to the environment and potential pathogens. Once infection has occurred, aspergillosis accounts for 74% of fatalities in lung transplant recipients. In addition, bone marrow transplant patients comprise the highest risk group with an 87% mortality rate following infection.

The most frequently used antifungal agents are polyenes, azoles and allylamines. Of these, amphotericin B and itraconazole have the broadest spectrum of activity against the most common of fungal infections: *Candida* spp. and *Aspergillus* spp. (Meis and Verweij, 2001). In the case of itraconazole, large interindividual differences in bioavailability are observed. (Grant and Clissold, 1989) due to its poor aqueous solubility (<1 μg/mL) and subsequent poor dissolution rate. Previous research by other groups has led to the development of alternative formulations for each of these drugs. U.S. Pat. No. 4,950,477 describes a method of preventing and treating pulmonary infection by fungi using aerosolized polyenes, e.g. amphotericin B, to treat aspergillosis. United States Publication 2004/0022862 A1 describes a method for preparing small particles, wherein the particles may be suitable for in vivo delivery by an administrative route such as pulmonary. US Publication 2003/0077329 A1 describes a composition and method for preparing stable particles in a frozen aqueous matrix, wherein such particles are suitable for pulmonary delivery. USPN 2003/0072807 A1 describes solid particulate antifungal compositions for pharmaceutical use, including pulmonary formulations of such compositions (but only a brief reference to pulmonary). US Publication 2002/0102294 A1 describes aerosols comprising nanoparticle drugs, and methods of using the formulations in aerosol delivery devices. U.S. Pat. No. 6,264,922 describes nebulized aerosols containing nanoparticle dispersions. WO 90/11754 describes aerosolized azole antifungals. However, none of these references specify that a particular lung concentration for an antifungal is desired, reached or maintained over a period of time. Nor do any of these references specify that a measure of inflammatory response is desired, reached or maintained, or that a particular blood concentration of pulmonary delivered antifungal is desired, reached or maintained. US Publication 2003/0068280 A1 teaches that certain antibiotics can have a residence time of over 12 hours, but this publication does not teach or describe anything relating to antifungal agents. United States Patent Publication 2004/0176391 A1 teaches specific lung concentrations and residence times specifically for Amphotericin B.

Recent research has led to the development of, e.g., lipid-based formulations of amphotericin B and numerous examples are reported in the literature for aerosolization of lipid-based formulations of Amphotericin B to treat fungal lung infections, but this approach has disadvantages because amphotericin B is poorly water soluble and poorly permeable across biological membranes. Research has also led to the incorporation of itraconazole into a cyclodextrin complex for intravenous and oral administration; however, there are side effects and toxicities that are associated with formulations including cyclodextrins, leading to upper limits on the dosages of such formulations that may not be sufficient for treatment. Moreover, cyclodextrins would have limited applicability for patients with reduced renal function, since cyclodextrins are cleared through the kidneys.

Given the broad spectrum of antifungal activity, it is clear that improvements in delivery of antifungal agents, such as itraconazole will lead to lower infection rates using prophylaxis treatment and lowered cost with more efficacious therapy. There is a clear medical need for a pulmonary formulation to supplement the currently available oral and intravenous formulations, based upon the results shown in this invention for targeted pulmonary delivery of an antifungal agent.

SUMMARY OF THE INVENTION

The compositions and methods of the present invention provide new dosage forms that enhance the delivery of one or more active agents or drugs. Advantageously, the present invention is able to overcome poor bioavailability of drugs for pulmonary delivery. The present invention is effective for treating local and systemic fungal/bacterial infections and can enable effective treatment of infection due to enhanced bioavailability. The present invention also has the potential advantage of macrophage-mediated lymphatic distribution.

The present invention also has the advantage of avoiding potential complications associated with systemic azole delivery, including drug interactions and hepatotoxicity.

In one aspect, the present invention is an inhalable composition comprising one or more respirable aggregates, the respirable aggregates comprising one or more poorly water soluble active agents, wherein at least one of the active agents reaches a maximum lung concentration ($C_{max}$) of at least about 0.25 µg/gram of lung tissue and remains at such concentration for a period of at least one hour after being delivered to the lung.

In another aspect, the present invention is a method of making one or more respirable aggregates comprising the steps of: mixing an effective ingredient with a solution agent; spraying the effective ingredient-solution agent mixture through an insulating nozzle located at or below the level of a cryogenic liquid, wherein the respirable aggregates deliver the active agent to the lung at a $C_{max}$ of at least about 0.5 µg/gram and wherein the active agent remains resident in the lung for at least about 2 hours.

In another aspect the present invention is a method of making one or more respirable aggregates comprising the steps of: dissolving a drug in at least one organic solvent to form a drug/organic mixture; spraying the drug/organic mixture via an atomizing device into an aqueous solution, wherein at least one particle stabilizer is originally present in the aqueous solution, the drug/organic mixture or both the aqueous solution and the drug/organic mixture, and wherein the drug/organic mixture is sprayed below the liquid level of the aqueous solution; and concurrently evaporating the organic solvent in the presence of the aqueous solution to form an aqueous dispersion of the drug particles, thereby causing the stabilizer to cover the drug particles as the organic solvent is evaporated, wherein the respirable aggregates deliver the active agent to the lung at a $C_{max}$ of at least about 0.5 µg/gram and wherein the active agent remains resident in the lung for at least about 2 hours.

In another aspect, the present invention is a method of making one or more respirable aggregates comprising the steps of: recirculating an anti-solvent through a mixing zone; dissolving the drug substance in a solvent to form a solution; adding the solution to the mixing zone to form a particle slurry in the anti-solvent; and recirculating at least a portion of the particle slurry back through the mixing zone, wherein the respirable aggregates deliver the active agent to the lung at a $C_{max}$ of at least about 0.5 µg/gram and wherein the active agent remains resident in the lung for at least about 2 hours.

In another aspect, the present invention is a method of making one or more respirable aggregates comprising the steps of: contacting a solution comprising a poorly water soluble drug substance and at least one freezable organic solvent with a cold surface so as to freeze the solution; and removing the organic solvent, wherein the respirable aggregates deliver the active agent to the lung at a $C_{max}$ of at least about 0.5 µg/gram and wherein the active agent remains resident in the lung for at least about 2 hours.

In another aspect, the present invention is a method of treating a respiratory infectious disease comprising the step of: administering an effective amount of respirable aggregates comprising a poorly water soluble active agent such that the active agent reach a $C_{max}$ in the lung of at least about 0.5 µg/g and maintain such concentration level for at least 2 hours.

In another aspect, the present invention is a pharmaceutical formulation that ameliorates a symptom of fungal disease comprising: at least one particle comprising a poorly water soluble active agent and a pharmaceutically-acceptable excipient suitable for pulmonary delivery disposed on or about a respirable particle, wherein the active agent achieves a maximum lung concentration of at least about 5 µg/g of lung tissue and maintains said maximum lung concentration for at least about 2 hours.

In another aspect, the present invention is a method for treating fungal disease in a subject in need of such treatment, comprising administering to the subject a pharmaceutically effective amount of at least one poorly water soluble antifungal agent effective to treat fungal disease in the subject, the antifungal agent being selected from the group consisting of natamycin, flucytosine, miconazole, fluconazole, itraconazole, clotrimazole, econazole, miconazole, ravuconazole, oxiconazole, sulconazole, terconazole, tioconazole, fenticonazole, bifonazole, oxiconazole, ketoconazole, isoconazole, tolnaftate, amorolfine, terbinafine, voriconazol, posaconazol, and the pharmacologically acceptable organic and inorganic salts or metal complexes or mixture thereof, in admixture with a pharmaceutically acceptable diluent or carrier, wherein the antifungal agent achieves a lung concentration of at least about 0.5 µg/g of tissue and maintains said maximum lung concentration for at least about 2 hours.

BRIEF DESCRIPTION OF THE DRAWINGS

For a more complete understanding of the features and advantages of the present invention, reference is now made to the detailed description of the invention along with the accompanying figures in which corresponding numerals in the different figures refer to corresponding parts and in which.

DETAILED DESCRIPTION OF THE INVENTION

Figure 1:
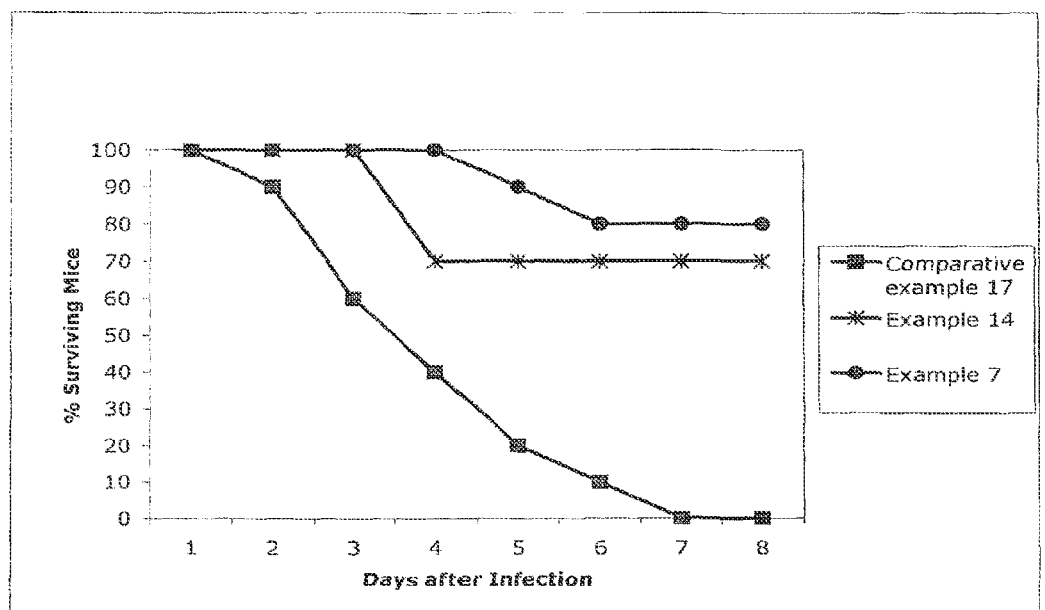
FIG. 1 is a graph that shows results from a survival/treatment study using some embodiments of the present invention.

While the making and using of various embodiments of the present invention are discussed in detail below, it should be appreciated that the present invention provides many applicable inventive concepts that may be embodied in a wide variety of specific contexts. The specific embodiments discussed herein are merely illustrative of specific ways to make and use the invention and are not to delimit the scope of the invention.

DEFINITIONS

As used herein the term "respirable aggregate" is used to describe an aggregate of one or more particles, the aggregate having a surface area (when in dry form) of greater than 1 $m^2/g$. More preferably, the surface area of the respirable aggregate is greater than about 5 $m^2/g$, even more preferably greater than about 10 $m^2/g$, and yet even more preferably greater than about 20 $m^2/g$. A respirable aggregate may also comprise smaller engineered active agent particles, each active agent particle having a particle size of less than about 1 μm. A respirable aggregate may be, for example a dry powder or a dry powder dispersed in liquid, forming one or more droplets. The respirable aggregates of the present invention are also easily wettable, as demonstrated by contact angle measurements for disks formed by pressing the respirable aggregates into tablet form. Such contact angle measurements are less than about 50 degrees, preferably less than 40 degrees, more preferably less than about 30 degrees, and even more preferably less than 20 degrees. Furthermore, the respirable aggregates of the present invention, when dry, have a porosity of at least about 10 percent, more preferably at least 25 percent, even more preferably at least about 40%, still more preferably at least 60% and up to about 80%. The respirable aggregates of the present invention demonstrate a density of from about 0.1 g/mL to about 5 g/mL.

As used herein the term "particle" is used to describe a particle comprising an active agent, such active agents being described below in more detail. The particles form individual units within a respirable aggregate, such that the respirable aggregate comprises one or more particles comprising the active agent, dispersed throughout the respirable aggregate.

The term "fine particle fraction" is defined to mean is the portion of the delivered material (i.e., a formulation that contains respirable aggregates and particles, either drops, dry powder, or the like) that actually is delivered to the lung. The fine particle fraction depends not only upon the performance of the particles and respirable aggregates, but also on the performance of the delivery device. This fine particle fraction will generally comprise respirable aggregates having a mass median aerodynamic diameter of between about 1 and about 5 μm. This is the desired size for the drops that are delivered for a nebulizer or pressurized metered dose inhaler (pMDI), or dry powder for a dry powder inhaler (DPI), such drops or powder comprising the aggregates and particles.

The terms "amount," "pharmaceutically effective amount" and "therapeutically effective amount" as used herein refer to a quantity or to a concentration as appropriate to the context. The amount of an active agent or drug that constitutes a pharmaceutically or therapeutically effective amount varies according to factors such as the potency of the particular drug, the route of administration of the formulation, and the mechanical system used to administer the formulation as will be known to the skilled artisan.

The term "treatment" or "treating" means any treatment of a disease in a mammal, including: (i) preventing the disease, that is, causing the clinical symptoms of the disease not to develop; (ii) inhibiting the disease, that is, arresting the development of clinical symptoms; and/or (iii) relieving the disease, that is, causing the regression of clinical symptoms.

As used herein the term "pharmaceutically acceptable carrier" includes any and all solvents, dispersion media, coatings, antibacterial and antifungal agents, stabilizing excipients, isotonic, absorption enhancing or delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

The term "immediate release" of the active agent from a nanoparticle as used herein describes a release profile to effect delivery of an active as soon as possible, that is, as soon as practically made available to an animal, whether in active form, as a precursor and/or as a metabolite of the agent provided.

As used herein the term "poorly water soluble" is defined as meaning that less than about 10 mg is soluble per mL water, and preferably less than about 1 mg/mL.

The term "solution" as used in this application is meant to include suspensions and emulsions, as well as solutions.

Respirable Aggregate and Particle Preparation

The respirable aggregates of the present invention are used to facilitate delivery of over 0.25 μg/g of an active agent to the deep lung. In certain embodiments delivery to the deep lung will be of at least about 1, 5, 10, 15, 20, 25 and even 30 μg/g of active agent in the lung tissue. The active agent is a poorly water soluble compound, that can also include a pharmaceutically acceptable carrier that affects its water-solubility. The respirable aggregates may even be separated from a mixture of fractions, respirable and non-respirable. The respirable aggregates stay in the lung (referred to herein as "residence time") for a period of at least about 2 hours, more preferably at least about 4 hours, even more preferably at least about 6 hours, still even more preferably at least about 8 hours, and most preferably at least about 12 hours.

The respirable aggregates of the present invention may be made using any suitable method known to those skilled in the art of preparing aggregated particles. Such methods include fast freezing methods, precipitation methods and emulsion methods. Preferred fast freezing methods are those referred to herein as spray freezing into liquid (SFL), as described in U.S. Pat. No. 6,862,890, incorporated herein by reference; and ultra-rapid freezing (URF), as described in US Publication No. 2004-0137070, incorporated herein by reference. An SFL method generally comprises the steps of mixing an effective ingredient with a solution agent; spraying the effective ingredient-solution agent mixture through an insulating nozzle located at or below the level of a cryogenic liquid, wherein the spray generates frozen particles. A URF method generally comprises the steps of contacting a solution comprising a poorly water soluble drug substance and at least one freezable organic solvent with a cold surface so as to freeze the solution; and removing the organic solvent.

Preferred precipitation methods are those referred to herein as evaporative precipitation into aqueous solution (EPAS), as described in U.S. Pat. No. 6,756,062, incorporated herein by reference; and controlled precipitation (CP), as described in U.S. Publication No. 2003-0049323, incorporated herein by reference. An EPAS method generally comprises the steps of dissolving a drug in at least one organic solvent to form a drug/organic mixture; spraying the drug/organic mixture into an aqueous solution; and concurrently evaporating the organic solvent in the presence of the aqueous solution to form an aqueous dispersion of the drug particles. A controlled precipitation method generally comprises the steps of recirculating an anti-solvent through a mixing zone, dissolving the drug substance in a solvent to form a solution, adding the solution to the mixing zone to form a particle slurry in the anti-solvent, and recirculating at least a portion of the particle slurry back through the mixing zone.

A preferred emulsion method includes those referred to herein as HIPE (high internal phase emulsions), as described in U.S. Pat. Nos. 5,539,021 and 5,688,842, incorporated herein by reference. A HIPE method generally comprises the steps of continuously merging into a disperser and in the presence of an emulsifying and a stabilizing amount of a surfactant, a continuous phase liquid stream having a flow rate $R_1$, and a disperse phase liquid stream having a flow rate $R_2$; and mixing the merged streams with a sufficient amount of shear, and with $R_2:R_1$ sufficiently constant, to form the high internal phase ratio emulsion without phase inversion or stepwise distribution of an internal phase into an external phase. These preferred methods create particles and respirable aggregates that are crystalline or amorphous in morphology. Advantageously, none of the preferred methods utilize mechanical milling or other similar unit operations that can cause thermal degradation of the active agent.

Inhalers and Nebulizers

Delivery of the respirable aggregates to the lung can be achieved through any suitable delivery means, including a nebulizer, a dry powder inhaler, or a metered dose inhaler. The most suitable delivery means will depend upon the active agent to be delivered to the lung, the desired effective amount for that active agent, and characteristics specific to a given patient. Those of ordinary skill in the art of pulmonary delivery will know the details of operating such devices. More information about the operation of such devices can also be found in, for example, "The Mechanics of Inhaled Pharmaceutical Aerosols: An Introduction", by W. H. Finlay, Academic Press, 2001; and in "Inhalation Aerosols" edited by A. J. Hickey, Marcel Dekker, New York, 1996, both of which are incorporated herein by reference.

Active Agents

Active agents suitable for use with the present invention are antifungal pharmaceuticals. Preferably, the active agent is an azole or an allylamine. Examples of antifungals useful with the present invention include, natamycin, flucytosine, miconazole, fluconazole, itraconazole, clotrimazole, econazole, miconazole, ravuconazole, oxiconazole, sulconazole, terconazole, tioconazole, fenticonazole, bifonazole, oxiconazole, ketoconazole, isoconazole, tolnaftate, amorolfine, terbinafine, voriconazol, posaconazol, and the pharmacologically acceptable organic and inorganic salts or metal complexes or mixture thereof. The active agent(s) of the present invention may be brought into solution using one or more organic solvents and/or a combination thereof. The organic solvents may be water miscible or water immiscible. Suitable organic solvents include but are not limited to: ethanol, methanol, tetrahydrofuran, acetonitrile, acetone, tert-butyl alcohol, dimethyl sulfoxide, N,N-dimethyl formamide, diethyl ether, methylene chloride, ethyl acetate, isopropyl acetate, butyl acetate, propyl acetate, toluene, hexanes, heptane, pentane, 1,3-dioxolane, isopropanol, n-propanol, propionaldehyde and combinations thereof.

Excipients and Adjuvants

The excipients and adjuvants that may be used in the present invention, while potentially having some activity in their own right, for example, antioxidants, are generally defined for this application as compounds that enhance the efficiency and/or efficacy of the active agents. It is also possible to have more than one excipient, adjuvant, or even active agent in a given solution. Non-limiting examples of compounds that may be included in the solutions that are to be made in accordance with the present invention include: surfactants, fillers, stabilizers, polymers, protease inhibitors, antioxidants and absorption enhancers. Excipients may be selected and added to either the drug/organic mixture or to the aqueous solution, either before or after the drug particles are formed, in order to enable the drug particles to be homogeneously admixed for appropriate administration. Suitable excipients include polymers, absorption enhancers, solubility enhancing agents, dissolution rate enhancing agents, stability enhancing agents, bioadhesive agents, controlled release agents, flow aids and processing aids. More particularly, suitable excipients include cellulose ethers, acrylic acid polymers, and bile salts. Other suitable excipients are described in detail in the Handbook of Pharmaceutical Excipients, published jointly by the American Pharmaceutical Association and The Pharmaceutical Society of Great Britain, the Pharmaceutical Press, 1986, relevant portions incorporated herein by reference herein. Such excipients are commercially available and/or can be prepared by techniques known in the art.

The excipients may also be chosen alone or in combination to modify the intended function of the effective ingredient by improving flow, or bio-availability, or to control or delay the release of the effective ingredient. Specific non-limiting examples include: Span 80, Tween 80, Brij 35, Brij 98, Pluronic, sucroester 7, sucroester 11, sucroester 15, sodium lauryl sulfate, oleic acid, laureth-9, laureth-8, lauric acid, vitamin E TPGS, Gelucire 50/13, Gelucire 53/10, Labrafil, dipalmitoyl phosphadityl choline, glycolic acid and salts, deoxycholic acid and salts, sodium fusidate, cyclodextrins, polyethylene glycols, labrasol, polyvinyl alcohols, polyvinyl pyrrolidones and tyloxapol, cellulose derivatives, and polyethoxylated castor oil derivatives. Using the process of the present invention, the morphology of the effective ingredients can be modified, resulting in highly porous particles and respirable aggregates.

Fungal Infections

The present invention can be used to treat a patient suffering from a fungal infection. Most common infections in this group are candidiasis and aspergillosis.

EXAMPLES

The following terms are used in the subsequent examples:

"1,3-dioxolane" is an organic solvent (Aldrich Chemical Company, Inc.).

"Brij 98" is a stabilizer that is a polyoxyethylene 20 oleyl ether (Sigma).

"CP" means controlled precipitation, a preferred method for making the particles and respirable aggregates of the present invention.

"Dichloromethane", sometimes referred to herein as "DCM", is an organic solvent.

"ELISA" is enzyme-linked immunosorbent assay.

"EPAS" means evaporative precipitation into aqueous solution, a preferred method for making the particles and respirable aggregates of the present invention.

"IL-12p70" is interleukin-12p70 isomer.

"ITZ" is itraconazole, an antifungal active agent (Hawkins, Inc.).

"Pluronic F-127" is poloxamer 407 stabilizer (Sigma).

"Polysorbate 20" and "Polysorbate 80" are stabilizers (Aldrich Chemical Company, Inc.).

"SFL" means spray freezing into liquid, a preferred method for making the particles and respirable aggregates of the present invention.

"SPORANOX" is a commercially available drug product containing intraconazole, intended for oral administration (Janssen)

"t-butanol" is an organic solvent (Fisher Scientific).

"Toluene" is an organic solvent (Fisher Scientific).

"URF" means ultra-rapid freezing, a preferred method for making the particles and respirable aggregates of the present invention.

"HIPE" means high internal phase emulsion, a preferred method for making the particles and respirable aggregates of the present invention.

Analytical Methods

The following analytical methods were used to characterize the particles and respirable aggregates of Examples 1-16 and Comparative Examples 17 and 18. Results are included with each enabling example.

Particle Size Analysis

After sonicating the samples for 30 seconds, particle size measurements for Examples 1-16 are conducted using Low angle laser light scattering with a Mastersizer S (Malvern Instruments Limited, Malvern, UK). Particle size measurements for Examples 19-23 were conducted using a Coulter LS230 (Beckman Coulter Corporation, Fullerton, Calif., USA).

Andersen Cascade Impaction for Aerodynamic Particle Size Analysis

Aerodynamic particle size analysis using Andersen Cascade Impaction is performed for Examples 2, 5, 10 and 13 according to USP guidelines.

Dissolution Testing

For Examples 1-10, dissolution testing is performed on the SFL powder samples (re-dispersed in water) using a USP 24 Type II paddle apparatus model VK7000 (Varian Inc., Palo Alto, Calif.). FIG. 1 depicts dissolution curves for Examples 1-16.

For Examples 19-23, dissolution testing is performed on the samples using a United States Pharmacopeia 24 Type 2 apparatus (Distek Dissolution System 210° C. with a TCS0200C heater/circulator; Crescent Scientific Pvt. Ltd.; Goregaon-East, Mumbai, India).

X-Ray Powder Diffraction (XRD)

The x-ray diffraction pattern for examples 1-16 and were analyzed using a model 1710 x-ray diffractometer (Philips Electronic Instruments, Inc., Mahwah, N.J.).

For Examples 19-23, X-ray powder diffraction is performed using a Siemens D-500 automated diffractometer equipped with a cobalt x-ray tube and a position sensitive detector. The result for Example 11 is substantially amorphous, Example 12 is substantially crystalline, and Examples 12-14 are substantially amorphous.

Surface Area Analysis

Surface area is measured using a Nova 2000 v.6.11 instrument (Quantachrome Instruments, Boynton Beach, Fla.).

Contact Angle Measurements

Tablets are pressed from the particles and respirable aggregates of the present invention (50 mg) using a Model M Carver Laboratory Press (Fred S. Carver, Inc., Menomonee Falls, Wis.) and a compression force of 300 kg. A droplet of dissolution media (3 μL) is placed on the flat face of the tablet and the contact angle is measured using a Model 100-00-115 goniometer (Rame-Hart Inc., Mountain Lakes, N.J.).

Example 1. Preparation of Particles and Respirable Aggregates Using an SFL Method SFL powders are prepared from a homogenous organic feed solution. The feed solution contains a 1:1 ratio of ITZ and polysorbate 80 dissolved in acetonitrile (0.3% w/v total solids). The feed solution is then atomized directly into liquid nitrogen to product frozen particles. The particles are separated from the liquid nitrogen, transferred to a non-insulated container and lyophilized using a VirTis Advantage Benchtop Tray Lyophilizer (VirTis Corp., Gardiner, N.Y.) equipped with a liquid nitrogen trap to condense sublimed organic solvents. The primary drying phase is performed at −40° C. for 24 hours. The shelf temperature is then ramped up at a rate of 0.9°/min to 25° C. where the secondary drying phase is conducted for a minimum of 12 hours. A vacuum of 200 mTorr is maintained for the primary drying phase and increased to 100 mTorr for the remainder of the freeze-drying cycle.

Mean particle size=20.7 μm; Dissolution=80% in 60 minutes; X-ray=amorphous; Surface area=1.38 $m^2$ $g^{-1}$.

Example 2. Nebulization of Respirable Aggregates Produced Using an SFL Method Particles from example 1 are re-dispersed in water to form a concentration of 20 mg/ml ITZ. The suspension is nebulized using an Aeroneb® Pro nebulizer (Aerogen Inc., Mountain view, Calif.) into an anderson cascade impactor equipped with a 1.8 L spacer. Total Emitted Dose (TED)=4170 μg; Fine particle fraction (FPF)=53.8%; Mass median aerodynamic diameter (MMAC)=2.76 μm; Geometric Standard Deviation (GSD)=2.1.

Example 3. Lung Residence Study of Respirable Aggregates Produced Using an SFL Method A suspension prepared as in example 2 is administered to seven-week old ICR/Swiss mice (Harlan-Sprague-Dawley, Indianapolis, Ind.), each weighing approximately 32 g and free of disease (prior to testing). Subjects (n=14) are housed in a modified anesthesia chamber and the suspension is aerosolized into the chamber using the same device as in example 2 to test the pulmonary efficacy of the ITZ formulation. Lungs are harvested from 2 separate mice at indicated time points in Table 1. Pharmacokinetic parameters calculated for lung residence data are: $C_{max}$=4.75±2.05 μg/g; $T_{max}$=1 hr; $K_d$=0.30 hrs$^{-1}$; $T_{1/2}$=2.28 hrs.

TABLE 1

| Time/hrs | Lung concentration (μg/g) | Standard Error |
| --- | --- | --- |
| 0.5 | 4.58 | 0.82 |
| 1 | 4.75 | 1.45 |
| 2 | 3.14 | 0.13 |
| 4 | 2.16 | 0.62 |
| 6 | 0.95 | 0.08 |
| 10 | <0.5 | — |
| 24 | <0.5 | — |

Example 4. Preparation of Particles and Respirable Aggregates Produced Using an SFL Method SFL powders are prepared as in Example 1, except that a homogenous feed solution is used instead of a feed emulsion, such that the feed solution contains a 1:0.75:0.75 ratio of ITZ, polaxomer 407 and polysorbate 80 dissolved in acetonitrile (0.3% w/v total solids). The feed solution is then atomized directly into liquid nitrogen to product frozen particles. Mean particle size=6.21 μm; Dissolution>80% in 5 minutes; X-ray=amorphous; Surface area 15.59 m$^2$ g$^{-1}$.

Example 5. Nebulization of Respirable Aggregates Produced Using an SFL Method The procedure described in example 2 is performed, except that particles from example 4 are used. Total Emitted Dose (TED)=125971 g; Fine particle fraction (FPF)=70.9%; Mass median aerodynamic diameter (MMAD)=2.82 μm; Geometric Standard Deviation (GSD)=1.7.

Example 6. Lung Residence Study of Respirable Aggregates Produced Using an SFL The procedure described in example 3 is followed, except that a suspension prepared as in example 5 is used and results are shown in Table 2.

TABLE 2

| Time/hrs | Lung concentration (μg/g) | Standard Error |
| --- | --- | --- |
| 0.5 | 9.9 | 0.54 |
| 1 | 13.4 | 0.47 |
| 2 | 9.9 | 1.02 |
| 4 | 8.5 | 0.18 |
| 6 | 4.8 | 0.17 |
| 10 | 1.5 | 0.08 |
| 24 | 0.76 | 0.03 |

Example 7. Prophylaxis/Prevention Study of Respirable Aggregates Produced Using an SFL Method Mice are dosed as in example 3, except that 10 mice are dosed and, instead of being sacrificed, they are dosed BID (twice a day) for 10 days to determine their survival. On the second day of dosing mice are immunosuppressed with corticosteroids and infected using spores of *Aspergillus fumigates*. Treatment is continued for the remaining 8 days. Results are illustrated in FIG. 1.

Figure 2:
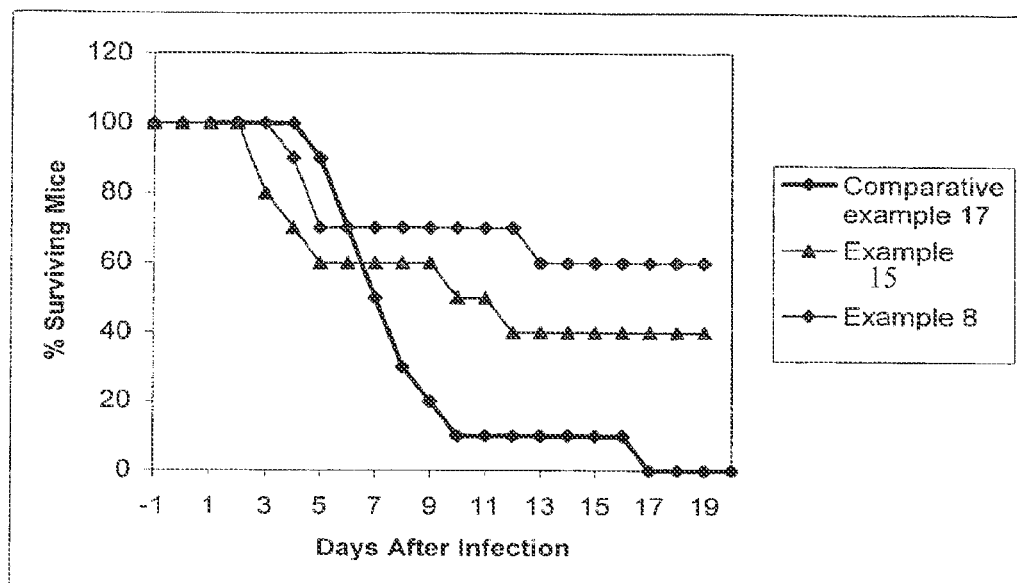
FIG. 2 is a graph that shows results from a survival/treatment study using some embodiments of the present invention.

Example 8. Survival/Treatment Study of Respirable Aggregates Produced Using an SFL Method Mice are treated as in example 7, except twice daily dosing is continued up to 14 days and further immunosuppression with corticosteroids is induced at day 10. Surviving mice are sacrificed at day 19. Results are illustrated in FIG. 2.

Example 9. Preparation of Particles and Respirable Aggregates Prepared Using an EPAS Method The EPAS particles and respirable aggregates are made as follows: ITZ (15 g) and poloxamer 407 (2 g) are dissolved in dichloromethane (100 mL) to produce an ITZ/organic feed solution. The ITZ/organic feed solution is heated (80° C.) and pumped (1 mL/min) under pressure through an atomizing nozzle (ΔP=20 MPa) directly into and below the liquid level of an aqueous solution (100 mL) comprising deionized water and a particle stabilizer (2% (w/v) Polysorbate 80). Dichloromethane is removed during processing to leave a dispersion of particles in an aqueous solution.

Example 10. Nebulization of Respirable Aggregates Produced Using an EPAS Method The procedure described in example 2 is followed, except that the particles and respirable aggregates already in suspension are used from example 9. Mean particle size=2.81 μm; TED=17426 μg; FPF=60.8%; MMAD=3.41 μm; GSD=2.2.

Example 11. Lung Residence Study of Respirable Aggregates Produced Using an EPAS Method The procedure described in example 3 is followed, except that a suspension from example 9 is used. Results are shown in Table 3. Pharmacokinetic parameters calculated for lung residence are: $C_{max}$=16.75±0.19 μg/g; $T_{max}$=0.5 hrs; $K_d$=0.16 hrs$^{-1}$; $T_{1/2}$=4.32 hrs.

TABLE 3

| Time/hrs | Lung concentration (μg/g) | Standard Error |
| --- | --- | --- |
| 0.5 | 16.75 | 0.13 |
| 1 | 15.61 | 2.96 |
| 2 | 8.11 | 1.15 |
| 4 | 6.12 | 0.97 |
| 6 | 4.16 | 0.37 |
| 10 | 2.28 | 0.40 |
| 24 | 1.33 | 0.03 |

Example 12. Preparation of Dry Powder from Particles and Respirable Aggregates Prepared Using an EPAS Method A suspension as prepared in example 9 is quench frozen in liquid nitrogen. This is then lyophilized as in example 1. Mean particle size=2.83 μm; Dissolution>80% in 2 minutes; X-ray=crystalline.

Example 13. Nebulization of Respirable Aggregates Produced Using an EPAS Method The procedure described in example 2 is followed, except that particles from example 12 are used.
TED=11011 μg; FPF=76%; MMAD=2.70 μm; GSD=1.9.

Example 14. Prophylaxis/Prevention Study of Respirable Aggregates Produced Using an EPAS Method The procedure described in example 7 is followed using the suspension from example 13. Results are illustrated in FIG. 1.

Example 15. Survival/Treatment Study of Respirable Aggregates Produced Using an EPAS Method The procedure described in example 8 is followed using the suspension from example 13. Results are illustrated in FIG. 2.

Example 16. Aerosolization of Respirable Aggregates Produced Using an SFL Method Particles prepared as in example 1 are dispersed using HFA 134a into a pressurized container. The resulting sample is actuated 5 times into an Anderson cascade impactor.
TED=286 µg; FPF=15%; MMAD=6.8 µm; GSD=2.6.

Comparative Example 17 Nebulized Control

Deionized water is nebulized using an Aeroneb Pro® nebulizer.

Comparative Example 18 Commercially Available Control

SPORANOX is administered orally to seven-week old ICR/Swiss mice (Harlan-Sprague-Dawley, Indianapolis. Ind.), each weighing approximately 32 g and free of disease (prior to testing). Fourteen Subjects (n=14) are used. Lungs are harvested from 2 separate mice at time points of 0.5, 1, 2, 4, 6, 10 and 24 hrs. No lung concentrations greater than 2.01 g/g are determined at any time point.

Example 19. Preparation of Particles and Respirable Aggregates Using a URF Method A solution of ITZ (0.0798 g) with pluronic F-127 (0.0239 g) is prepared by loading the dry solids into a vial. A prepared 95/5 wt % blend of t-butanol and toluene (10.03 g) is loaded into the vial. The resulting slurry is heated until a solution was formed. (68 to 70° C.). The resulting solution is applied to the freezing surface of the URF unit, which had been cooled to −78° C. over a three-minute time period. The frozen solvent, drug, and excipient matrix is collected in a tray, which had been cooled with dry ice, and transferred into a 60-mL jar, which had been cooled with dry ice. The jar containing the URF processed frozen solid is then placed on a freeze drying unit and lyophilized for approximately 17 hr at 100 mtorr. After lyophilization, 0.0700 g of the URF processed solid is recovered as a dry flowable powder. The mean volume average particle sizes (with and without sonication) of the reconstituted drug particles are measured using a Coulter LS 230. The particles are amorphous.

Example 20. Preparation of Particles and Respirable Aggregates Using a Controlled Precipitation (CP) Method A batch controlled precipitation process is used. An aliquot of 1.77 grams of Brij 98 is dissolved in 148.33 grams of deionized water. The aqueous solution is then recirculated, using a centrifugal pump (Cole-Parmer Model 75225-10) at maximum pump speed (9000 rpm), through recirculation loop 17 and through heat exchanger 23 (Exergy Inc. Model 00283-01, 23 series heat exchanger) until the aqueous temperature is 5° C. An aliquot of 30.19 grams of a solution containing 5 wt % ITZ in 1,3-dioxolane is added into the recirculating aqueous solution over about 25 seconds, which results in the controlled precipitation of a particle slurry. The particle size of the particle slurry is measured, without filtration or sonication, using a Coulter LS 230. The particle slurry is then fed to a wiped-film evaporator having a jacket temperature of 40° C., an absolute pressure of 8 mm Hg, and a feed rate of 15 mL/min. The particle size of the solvent-stripped slurry is measured, without filtration or sonication, using a Coulter LS 230.

The stripped slurry from Example 20 is freeze-dried for about 48 hours with an Edwards vacuum pump operated at maximum vacuum to isolate the drug particles. The particles are crystalline. The drug particles are reconstituted by dispersing with deionized water to a level of about 1-2 wt % solids and vortexing. The mean volume average particle size of the reconstituted freeze-dried drug particles is 2.67 µm, as measured, without filtration or sonication, using a Coulter LS 230.

Example 21. Particles and Respirable Aggregates Prepared Using an Emulsion Method A 2.0 g aliquot of ITZ is dissolved in 23.0 g of methylene chloride to produce an organic solution. This solution becomes the dispersed phase. The continuous phase consists of 12.5 grams of 2% aqueous sodium dodecyl sulfate (SDS) solution. The aqueous-organic solutions are shaken together by hand to form a crude emulsion.

The emulsion is homogenized using a Fisher PowerGen 700D variable-speed motor with 20-mm dia. generator (rotor/stator) assembly for 30 to 60 seconds at 20,000 rpm. A 20.0 g aliquot of 5% Methocel E3 aqueous solution is added to the emulsion along with 16.3 grams of deionized water during homogenization. Methylene chloride is removed from the resulting mixture. The resulting suspension is freeze-dried to form a powder comprising amorphous particles.

Each isolated powder is redispersed in deionized water at 1-2 wt % to form a slurry for particle size analysis. The particle size of the slurry is measured, without filtration or sonication, using a Coulter LS 230.

Examples 22-23. Particles and Respirable Aggregates Prepared Using an Emulsion Method Two other samples are prepared using the same procedure in Example 21, except sodium oleate is used instead of SDS. All isolated powders have nondetectable residual methylene chloride levels and comprise amorphous particles.

TABLE 4

Materials Used in Emulsion Examples 22 and 23

| Materials | Example 22 | Example 23 |
|---|---|---|
| ITZ | 2.0 | 6.0 |
| Methylene chloride | 23.0 | 69.0 |
| 2% Aqueous Sodium Oleate | 12.5 | 37.5 |
| 5% Aqueous Methocel E3 | 20.0 | 60.0 |
| Deionized water | 15.0 | 45.0 |

Comparative Example 24

The material used in this example comprises an aqueous suspension of micronized itraconazole (bulk itraconazole) with polysorbate 80 in a weight ratio of 9:1 (1 mg/mL w/v total solids).

Comparative Example 25

The material used in this example comprises bulk ITZ, unprocessed and in dry powder form, for use as a comparison with the particles and respirable aggregates of the present invention.

TABLE 5

Dissolution times for Examples 20-23 and comparative example 25

| Example | | Percent Dissolved at Time Points in Minutes Time | | | | | | | | |
|---|---|---|---|---|---|---|---|---|---|---|
| | | 2 | 5 | 10 | 15 | 20 | 25 | 30 | 60 | 120 |
| 21 | Avg | 100.2% | 100.7% | 100.3% | 101.5% | 99.6% | 98.8% | 100.1% | 99.3% | 100.0% |
| | σ | 3.6% | 2.4% | 2.4% | 3.1% | 2.4% | 3.1% | 2.9% | 3.4% | 2.7% |
| 20 | Avg | 33.9% | 54.2% | 68.4% | 74.0% | 77.9% | 80.3% | 83.0% | 86.8% | 99.9% |
| | σ | 2.8% | 5.8% | 6.3% | 5.3% | 4.7% | 4.0% | 4.1% | 4.0% | 6.9% |
| 22 | Avg | 20.2% | 26.6% | 33.4% | 39.7% | 45.0% | 49.7% | 54.5% | 68.0% | 100.0% |
| | σ | 3.1% | 4.0% | 5.4% | 6.6% | 7.8% | 8.8% | 9.8% | 10.8% | 4.4% |
| 23 | Avg | 22.9% | 32.1% | 37.3% | 39.9% | 42.2% | 44.7% | 47.2% | 61.3% | 100.0% |
| | σ | 2.0% | 2.6% | 2.6% | 3.0% | 3.4% | 4.6% | 5.6% | 10.1% | 5.2% |
| 25 (comp) | Avg | 3.1% | 4.8% | 9.1% | 12.7% | 15.5% | 18.2% | 19.7% | 38.9% | 100.0% |
| | σ | 0.1% | 0.7% | 2.1% | 3.2% | 4.1% | 4.6% | 5.0% | 7.7% | 4.2% |

Examples 26 and 27: ITZ Single Dose Pharmacokinetics in Lung Tissue and in Serum and Calculated Pharmacokinetic Parameters Following Pulmonary Administration of an ITZ Formulation Male Harlan-Spague-Dawley ICR mice (Hsd:ICR, Harlan Sprague Dawley, Inc., Indianapolis, Ind.) are dosed with ITZ-pulmonary formulation used in Example 3 using a dosing chamber.

Figure 3:
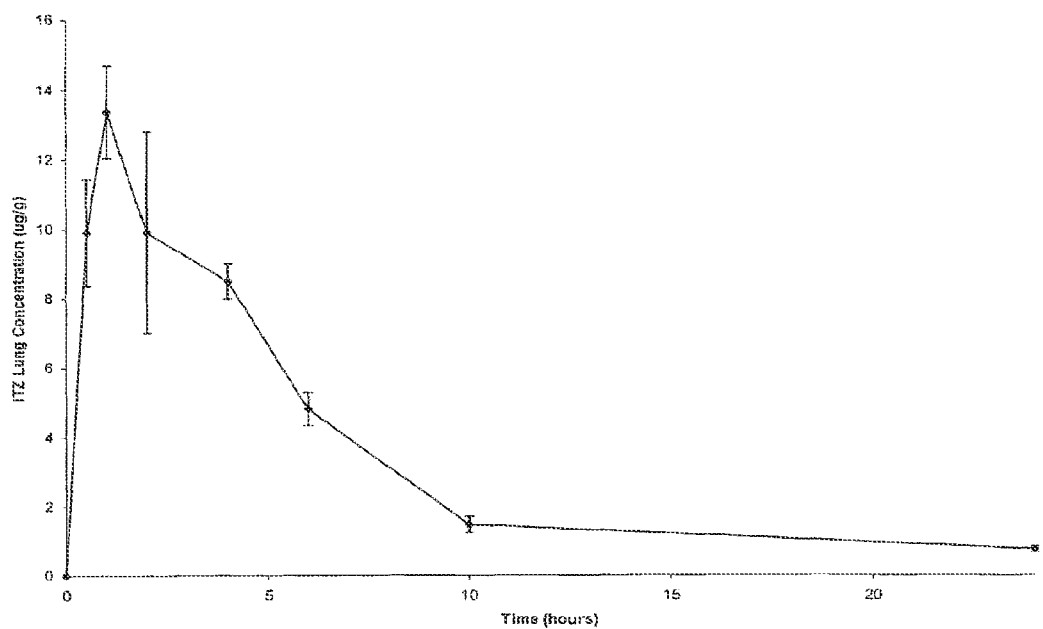
FIG. 3 is a graph depicting lung tissue concentrations in mice according to an embodiment of the present invention. Average ITZ lung tissue concentrations in mice dosed with ITZ-pulmonary. N=2 mice per time point with 4 individual extractions from each mouse.
Figure 4:
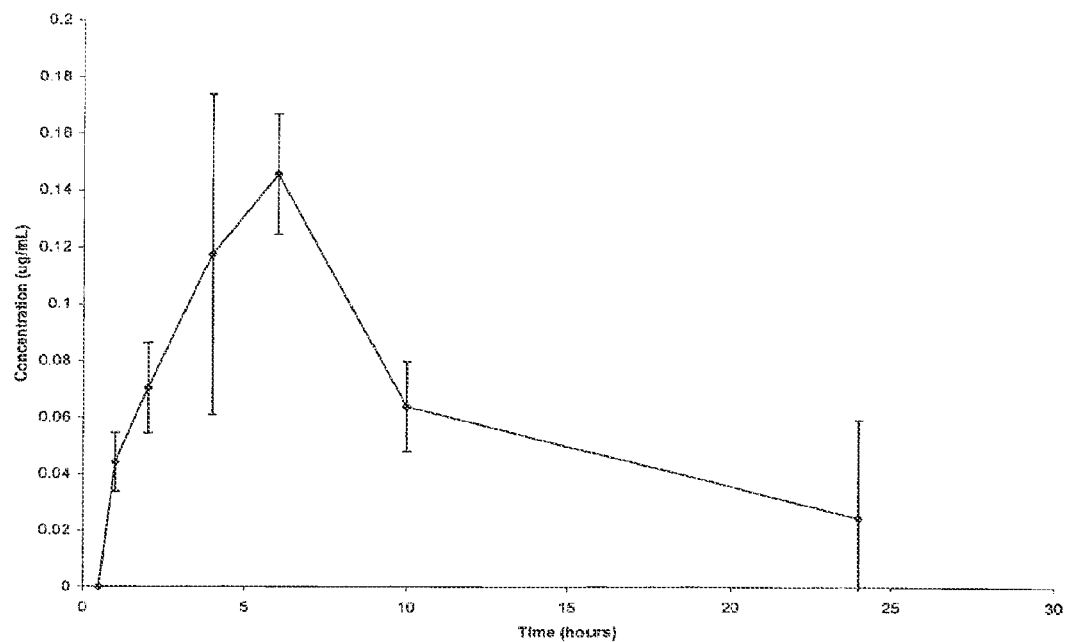
FIG. 4 is a graph depicting average serum concentrations for mice according to an embodiment of the present invention. Average ITZ serum concentrations over a 24 hour period for mice dosed with ITZ-pulmonary. N=2 mice per time point.

A 20 mg/mL ITZ-pulmonary dispersion was formed in 4 mL of normal saline. An AERONEB PRO micro pump nebulizer (Aerogen, Inc., Mountain View, Calif.) was situated at the inlet of the chamber and nebulization of 8 mL aliquots of the ITZ pulmonary dispersion was conducted over 20 minutes for each dose. For the 24 hr pharmacokinetic study, two mice were sacrificed by carbon dioxide narcosis at each time point (0.5, 1, 2, 4, 6, 10, 24 hours), and their serum was collected and lungs were extracted and both analyzed for ITZ content. The lung pharmacokinetic curve is shown in FIG. 3.

TABLE 7

Pharmacokinetic parameters for lung and serum concentrations from mice dosed with the amorphous ITZ pulmonary composition.

| Pharmacokinetic Parameter | Lung$^\alpha$ | Serum$^\beta$ |
|---|---|---|
| $C_{max}$ (μg/g) | 13.4 | 0.12 |
| $T_{max}$ (hrs) | 1 | 5.35 |
| $T_{1/2\ K01}$ (hrs) | | 3.73 |
| $T_{1/2\ K10}$ (hrs) | 5.5 | 3.70 |
| $K_{01}$ (hrs$^{-1}$) absorption | | 0.186 |
| $K_{10}$ (hrs$^{-1}$) elimination | 0.13 | 0.188 |
| $AUC_{inf}$ (μg · h/mL) | 85.8 | 1.69 |

$^\alpha$Based on non-compartmental analysis of the lung tissue concentrations vs. time.
$^\beta$Calculated based on one-compartmental analysis of the serum concentrations vs. time for extravascular administration.

Comparative Example 28: Toxicity Associated with Multiple Oral Dosing of SPORANOX Oral Solution Mice were dosed with 30 mg/kg by oral dosing of SPORANOX every twelve hours for up to twelve days. Observations were conducted to determine the health of mice which were administered multiple doses.

Example 29: Toxicity Associated with Pulmonary Administration of ITZ Pulmonary Formulation Mice were dosed with 30 mg/kg through pulmonary administration of a pulmonary ITZ formulation every twelve hours for up to twelve days. Observations were conducted to determine the health of mice which were administered multiple doses.

TABLE 8

Morphological observations in mice dosed with ITZ-pulmonary and with the Sporanox ® oral solution; (+) symptoms were observed in mice from that group; (−) no symptoms were observed.

| | Example 29 | Comparative Example 28 |
|---|---|---|
| Dose related deaths$^\Phi$ | 0 | 2 |
| Evidence of dehydration$^\alpha$ | − | + |
| Diarrhea$^\beta$ | − | + |
| Decreased grooming$^\chi$ | − | + |
| Dosing resistance$^\delta$ | − | + |

$^\Phi$Indicates the total number of deaths during the study period
$^\alpha$Mice displayed poor skin turgor upon scruffing during dosing and were lethargic.
$^\beta$Diarrhea was evident by moist and watery stool.
$^\chi$Decreased grooming was noted as fur which was unkempt and soiled.
$^\delta$Immediate resistance to dosing upon insertion of the gavage tip into the oral cavity.

Example 30: Multiple Dose Trough Levels for ITZ Delivered Via Pulmonary Administration Mice were dosed with 30 mg/kg through pulmonary administration of a pulmonary ITZ formulation every twelve hours for up to twelve days. Twelve hours after the last dose (trough levels) on days 3, 8 and 12, four mice were sacrificed by carbon dioxide narcosis. Blood was collected by cardiac puncture, allowed to clot for 20 min, centrifuged and serum was collected. Surgery was performed on each mouse to extract the lung tissue which was then homogenized in 1 mL of normal saline and four 0.25 mL aliquots were analyzed for ITZ by reverse phase high performance liquid chromatography (HPLC).

Comparative Example 31: Multiple Dose Trough Levels for Oral Dosing of SPORANOX Mice were dosed with 30 mg/kg by oral dosing of SPORANOX every twelve hours for up to twelve days. Twelve hours after the last dose (trough levels) on days 3, 8 and 12, four mice were sacrificed by carbon dioxide narcosis. Blood was collected by cardiac puncture, allowed to clot for 20 min, centrifuged and serum was collected. Surgery was performed on each mouse to extract the lung tissue which was then homogenized in 1 mL of normal saline and four 0.25 mL aliquots were analyzed for ITZ by reverse phase high performance liquid chromatography (HPLC).

TABLE 9

Trough levels of ITZ in lung and serum from mice dosed with a commercial ITZ by oral delivery and an ITZ formulation by pulmonary delivery.

| | Average Lung Concentrations (ug/g) | | | Average Serum Concentrations (ug/g) | | | Lung:Serum Ratio | | |
|---|---|---|---|---|---|---|---|---|---|
| Day | 3 | 8 | 12 | 3 | 8 | 12 | 3 | 8 | 12 |
| Example 30 | 2.16 | 2.22 | 2.52 | 0.12 | 0.11 | 0.11 | 18.15 | 20.18 | 22.27 |
| Comparative Example 31 | 0.19 | 0.15 | 0.18 | 0.31 | 0.37 | 0.39 | 0.61 | 0.40 | 0.45 |

Example 32: Inflammatory Response to the Administration of Itz to the Lungs

Figure 5:
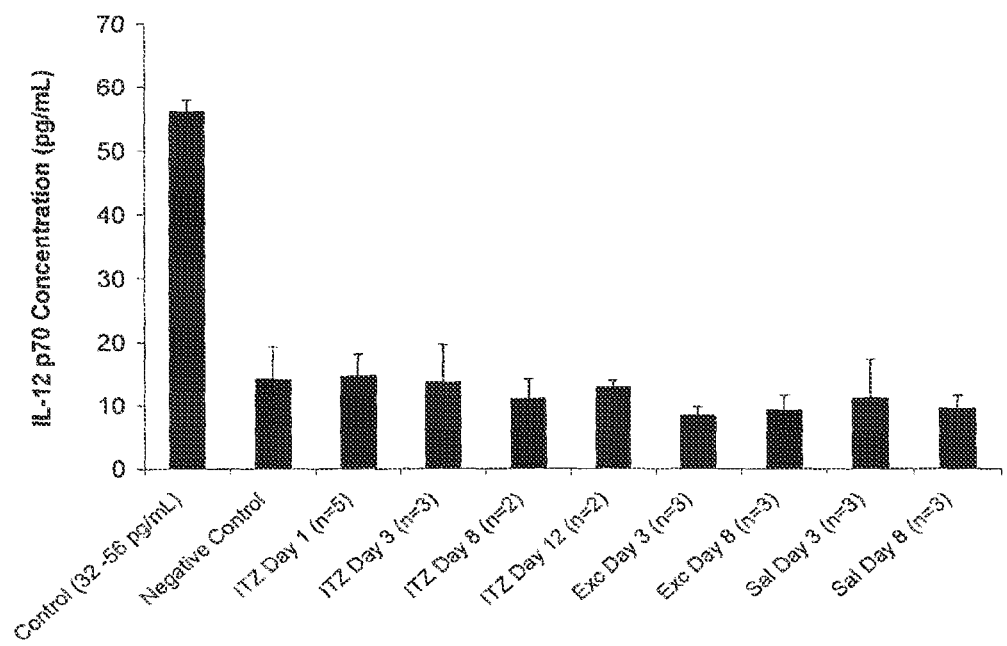
FIG. 5 is a chart depicting lung concentration levels of IL-12p70 for an embodiment of the present invention. Mean IL-12p70 concentrations measured according to Example 32 via ELISA assay of the positive control, negative control and BAL supernatants of sacrificed mice.

Surgery was performed on sacrificed mice to expose the pleural cavity and trachea at the throat. A small incision was cut into the trachea and a cannula consisting of a 23 gauge needle with a sheath of plastic tubing (0.037" outside diameter (OD) and 0.025" ID) was inserted through the incision to the base of the trachea and clamped to seal the opening. An aliquot (0.75 mL) of phosphate buffered saline was instilled through the cannula into the lungs and then removed to wash the bronchial and alveolar surfaces. This process was repeated for a total of three washes. The phosphate buffered saline containing cells was placed into centrifuge vials and centrifuged at 300 rpm (MiniSpin Plus. Eppendorf International, Hamburg, Del.). The supernatant was removed leaving the collected cells in the pellet. The supernatant from the BAL (Bronchoalveolar Lavage) was analyzed by enzyme-linked immunosorbent assay (ELISA) for IL-12 elevation (n=2 per sample tested). Because administration of ITZ does not result in IL-12 elevation, ITZ does not appear to cause inflammation of the lung, as shown in FIG. 5, as compared to the excipients alone and the saline solution.

Example 33: Histological Analysis of Mouse Lungs Dosed with Pulmonary ITZ

Mice which were dosed via inhalation for up to 8 days with an ITZ formulation and were evaluated for histological changes and scored according to the Cimolai histopathologic scoring system. Lungs were harvested and placed into 10% formaldehyde followed by processing and embedding into paraffin wax. Coronal sections of the entire lung were stained and viewed by light microscopy. The Cimolai histopathologic inflammatory score of 0-26 was obtained for each lobe.

Comparative Example 34: Histological Analysis of Mouse Lungs Dosed with Excipient Placebo Mice which were dosed via inhalation for up to 8 days with a formulation consisting of substantially the same formulation as in example 33, except without the ITZ, and were evaluated for histological changes and scored according to the Cimolai histopathologic scoring system. Lungs were harvested and placed into 10% formaldehyde followed by processing and embedding into paraffin wax. Coronal sections of the entire lung were stained and viewed by light microscopy. The Cimolai histopathologic inflammatory score of 0-26 was obtained for each lobe.

Comparative Example 35: Histological Analysis of Mouse Lungs Dosed with a Saline Control Mice which were dosed via inhalation for up to 8 days with saline solution (0.9% saline) and were evaluated for histological changes and scored according to the Cimolai histopathologic scoring system. Lungs were harvested and placed into 10% formaldehyde followed by processing and embedding into paraffin wax. Coronal sections of the entire lung were stained and viewed by light microscopy. The Cimolai histopathologic inflammatory score of 0-26 was obtained for each lobe.

TABLE 10

Cimolai histopathologic inflammatory score of mice dosed via inhalation with an ITZ composition, excipient placebo or a saline control

| | Example 33 | Comparative Example 34 | Comparative Example 35 |
|---|---|---|---|
| Day 3 | 2.4 | 2.25 | 3.0 |
| Day 8 | 3.3 | 2.7 | 3.6 |

Example 36: Macrophage Uptake of ITZ which was Dosed Via Pulmonary Administration Cells (airway macrophages) were recovered from the lung and subjected to drug extraction and analyzed by mass spectroscopy for confirmation of ITZ presence in the macrophage. Samples taken on days 1, 3, 8, and 12 all showed the presence of ITZ.

The invention claimed is:

1. An inhalable composition comprising porous, respirable nanoparticle aggregates suitable for deep lung deposition, the aggregates comprising one or more active antifungal agents, wherein at least one of the active agents reaches a maximum lung concentration ($C_{max}$) of at least 0.25 μg/gram of lung tissue and remains at such concentration for a period of at least two hours after being delivered to the lung.

2. The composition of claim 1, wherein the respirable nanoparticle aggregates have a mass median aerodynamic diameter of from about 1 μm and about 5 μm.

3. The composition of claim 1, wherein the respirable nanoparticle aggregates have a density from about 0.1 g/mL to about 5 g/mL.

4. The composition of claim 1, wherein one or more antifungal agents is an azole antifungal.

5. The composition of claim 1, wherein the antifungal agent is natamycin, flucytosine, miconazole, fluconazole, itraconazole, clotrimazole, econazole, miconazole, ravuconazole, oxiconazole, sulconazole, terconazole, tioconazole, fenticonazole, bifonazole, oxiconazole, ketoconazole, isoconazole, tolnaftate, amorolfine, terbinafine, voriconazol, posaconazol, or the pharmacologically acceptable organic and inorganic salts or metal complexes or mixture thereof.

6. The composition of claim 1, wherein aggregates comprised in the composition have a porosity of from 10 percent to 80 percent.

7. The composition of claim 6, wherein the aggregates have a porosity of at least 40 percent.

8. The composition of claim 7, wherein the aggregates have a porosity of at least 60 percent.

9. The composition of claim 1, wherein aggregates comprised in the composition have a surface area of greater than 1 $m^2/g$.

10. The composition of claim 1, wherein the respirable nanoparticle aggregates are prepared by a process comprising ultra-rapid freezing of amorphous antifungal drug solubilized in a freezable solvent on a solid substrate to form the respirable nanoparticle aggregates.

* * * * *